(12) United States Patent
Morgan

(10) Patent No.: US 6,610,080 B2
(45) Date of Patent: Aug. 26, 2003

(54) PARABOLIC EYELET SUTURE ANCHOR

(75) Inventor: Daniel E. Morgan, Salem, MA (US)

(73) Assignee: Axya Medical, Inc., Beverly, MA (US)

( * ) Notice: Subject to any disclaimer, the term of this patent is extended or adjusted under 35 U.S.C. 154(b) by 0 days.

(21) Appl. No.: 10/017,104

(22) Filed: Dec. 14, 2001

(65) Prior Publication Data

US 2002/0120292 A1 Aug. 29, 2002

Related U.S. Application Data (60) Provisional application No. 60/272,218, filed on Feb. 28, 2001.

(51) Int. Cl.[7] ............................................. A61B 17/04
(52) U.S. Cl. ........................... 606/232; 606/72; 606/74; 606/218
(58) Field of Search ...................... 606/72, 218, 232, 606/74, 53; 411/422, 426

(56) References Cited

U.S. PATENT DOCUMENTS

| | | | |
|---|---|---|---|
| 5,891,146 A | 4/1999 | Simon et al. | |
| 5,951,560 A | 9/1999 | Simon et al. | |
| 6,007,566 A | * 12/1999 | Wenstrom, Jr. | ............. 606/232 |
| 6,086,608 A | * 7/2000 | Ek et al. | ............. 606/232 |
| 6,139,565 A | 10/2000 | Stone et al. | |
| 6,168,598 B1 | * 1/2001 | Martello | ............. 606/74 |
| 6,210,376 B1 | * 4/2001 | Grayson | ............. 604/264 |
| 6,264,677 B1 | 7/2001 | Simon et al. | |
| 6,267,766 B1 | 7/2001 | Burkhart | |
| 6,290,700 B1 | * 9/2001 | Schmotzer | ............. 606/61 |
| 6,436,124 B1 | * 8/2002 | Anderson et al. | ............. 606/232 |

* cited by examiner

*Primary Examiner*—Michael J. Milano
*Assistant Examiner*—Gwen Phanijphand
(74) *Attorney, Agent, or Firm*—McDermott, Will & Emery (57) ABSTRACT

A suture anchor for securing soft tissue to bone including a body extending along a longitudinal axis between opposite ends, and at least one eyelet extending between lateral surfaces of the body for receiving a suture. The eyelet defines two entry/exit void regions and a central void region extending between the entry/exit void regions. Each entry/exit void region extends from one of the lateral surfaces of the body and has an axis forming an acute angle with the longitudinal axis of the body. Each entry/exit void region also has a surface comprising a segment of a conic surface extending about the axis of the entry/exit void region and tapering inward towards the longitudinal axis of the body. The central void region extends along an axis transverse to the longitudinal axis of the body.

43 Claims, 9 Drawing Sheets

PARABOLIC EYELET SUTURE ANCHOR

CROSS-REFERENCE TO RELATED APPLICATION

The present application claims priority to provisional U.S. patent application serial No. 60/272,218, filed on Feb. 28, 2001, which is assigned to the assignee of the present application and incorporated herein by reference.

BACKGROUND OF DISCLOSURE

1. Field of Disclosure

The present disclosure relates to anchors for securing surgical suture to bone. More specifically, the present disclosure relates to arthroscopic apparatus and methods for anchoring suture to bone using an anchor preferably having an eyelet formed to reduce or eliminate damage to the suture associated with passing the suture through the eyelet.

2. Description of Related Art

When soft tissue tears away from bone, reattachment becomes necessary. Various devices, including sutures alone, screws, staples, wedges, and plugs have been used to secure soft tissue to bone. Various types of suture anchors have been developed for this purpose. Some suture anchors are designed to be inserted into a pre-drilled hole, while other suture anchors are threaded and self-tapping. Some suture anchors include an eyelet for receiving a suture, while other anchors are cylindrical and adapted for holding a knotted piece of suture, while still other anchors include a strand of suture insert molded in the anchor.

What is still desired, however, is an improved suture anchor for use in reattaching soft tissue to bone. Preferably, the improved suture anchor will include at least one eyelet for receiving a surgical suture and which allows a relatively large angle of entry and a gentle lead in for a suture threaded through the eyelet, while minimizing damage to the suture. What are also desired are arthroscopic apparatus and methods for anchoring suture to bone using such an anchor, and wherein the apparatus and methods themselves are adapted to minimize damage to a suture threaded through the eyelet of the anchor.

SUMMARY OF THE DISCLOSURE

The present disclosure provides a suture anchor for securing soft tissue to bone, including a body extending from a proximal end to a distal end along a longitudinal axis, and at least one eyelet extending between opposite lateral surfaces of the body for receiving a suture. The eyelet defines two entry/exit void regions and a central void region extending between the entry/exit void regions along an axis extending transverse to the longitudinal axis of the body. Each entry/exit void region extends from one of the lateral surfaces of the body, has an axis forming an acute angle with the longitudinal axis of the body, and has a surface comprising a segment of a conic surface extending about the axis of the entry/exit void region and tapering inward towards the longitudinal axis of the body.

The present design of the eyelet allows for greater angles of suture entry, a gentle lead in and minimal damage to a suture thread passed through the eyelet.

Other features and advantages of the present disclosure will become apparent from the following detailed description and the accompanying drawings.

BRIEF DESCRIPTION OF THE DRAWINGS

Like reference characters designate identical or corresponding components and units throughout the several views.

DETAILED DESCRIPTION OF THE PREFERRED EMBODIMENTS

Figure 1:
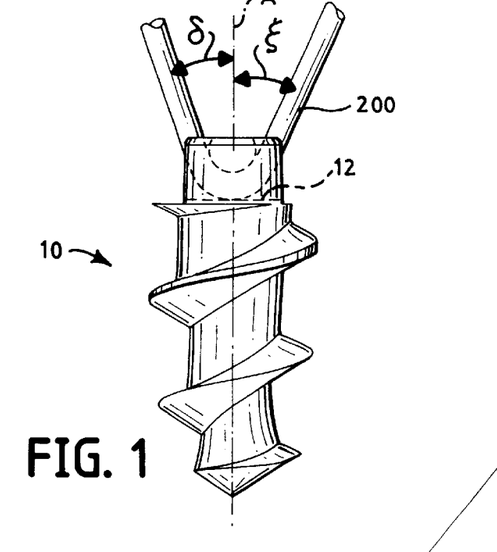
FIG. 1 is a side elevation view of a suture anchor constructed in accordance with the present disclosure.
Figure 2:
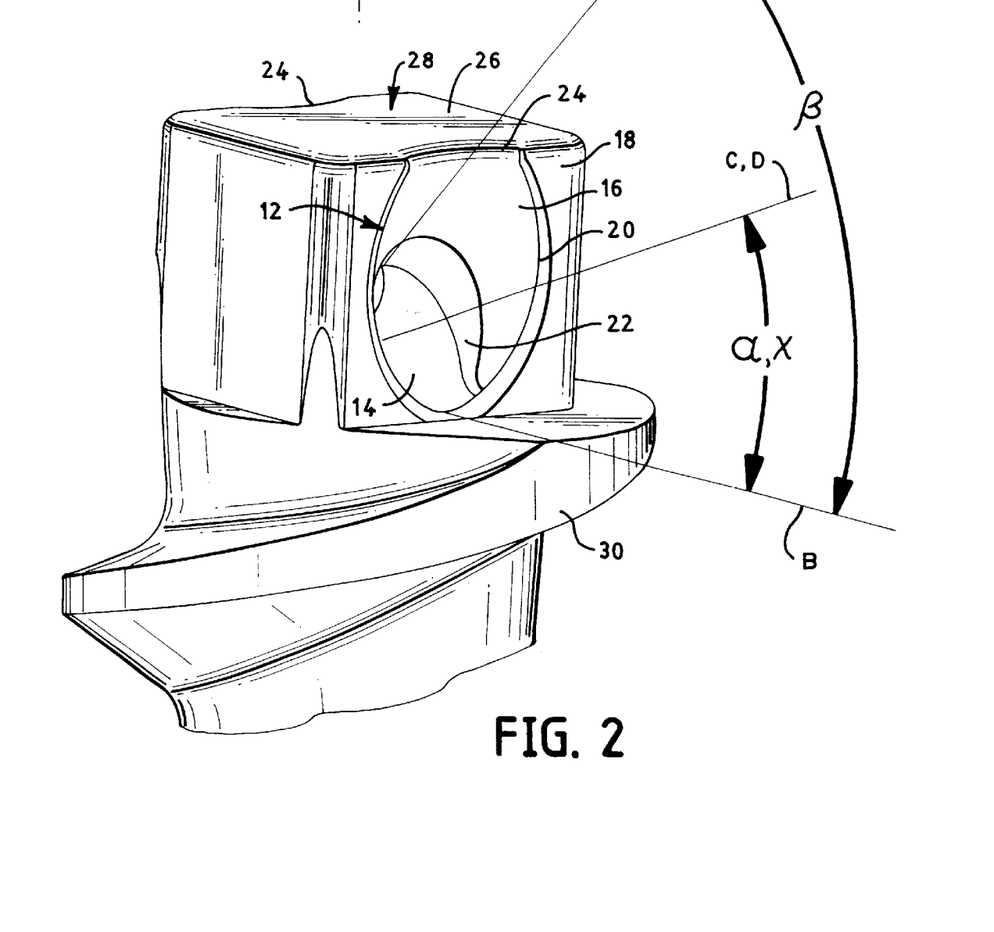
FIG. 2 is an enlarged perspective view of a portion of the suture anchor of FIG. 1.

Referring to FIGS. 1 through 5, a suture anchor 10 constructed in accordance with the present invention is shown. The suture anchor 10 includes an eyelet 12 for securing a length of suture 200 to bone (not shown), which in turn, can be secured around or through soft tissue (not shown) to secure the soft tissue to the bone. The anchor 10 can be used with many types of bio-compatible sutures including monofilament sutures, braided sutures, absorbable sutures, and non-absorbable sutures. The presently disclosed suture anchor 10 allows for a gentle lead in and minimal damage to a suture threaded through the eyelet 12, especially when an entry angle "δ" and an exit angle "ε" of the suture 200 are each about forty-five degrees with respect to a longitudinal axis "A" of the anchor 10, as shown in FIG. 1.

Figure 3:
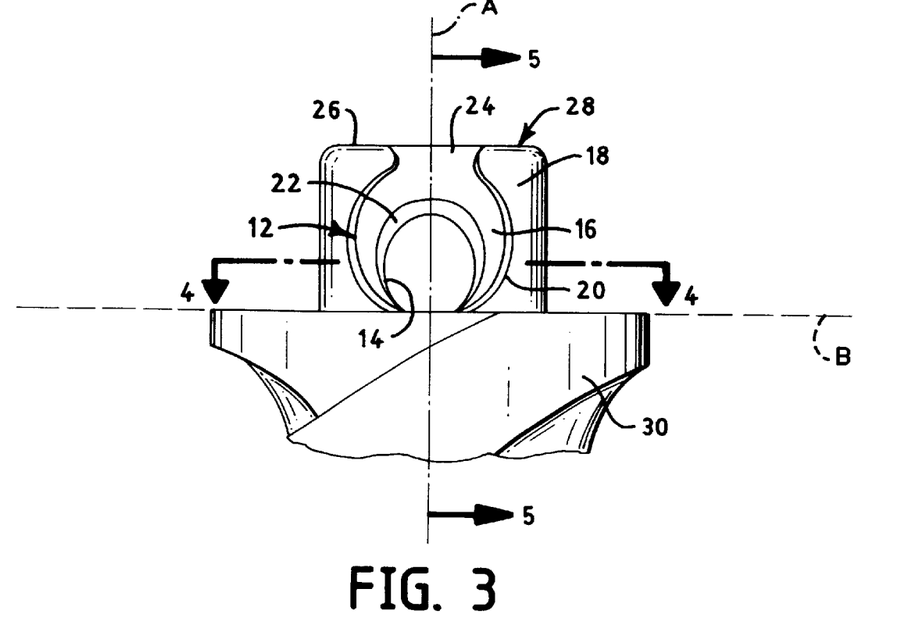
FIG. 3 is an elevation view of a portion of the suture anchor of FIG. 1.
Figure 4:
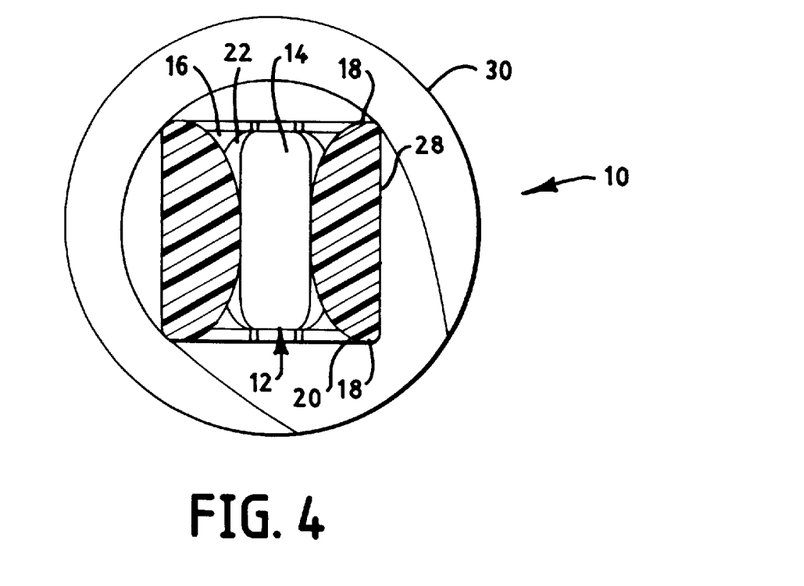
FIG. 4 is a sectional view of the suture anchor of FIG. 1 taken along line 4—4 of FIG. 3.
Figure 5:
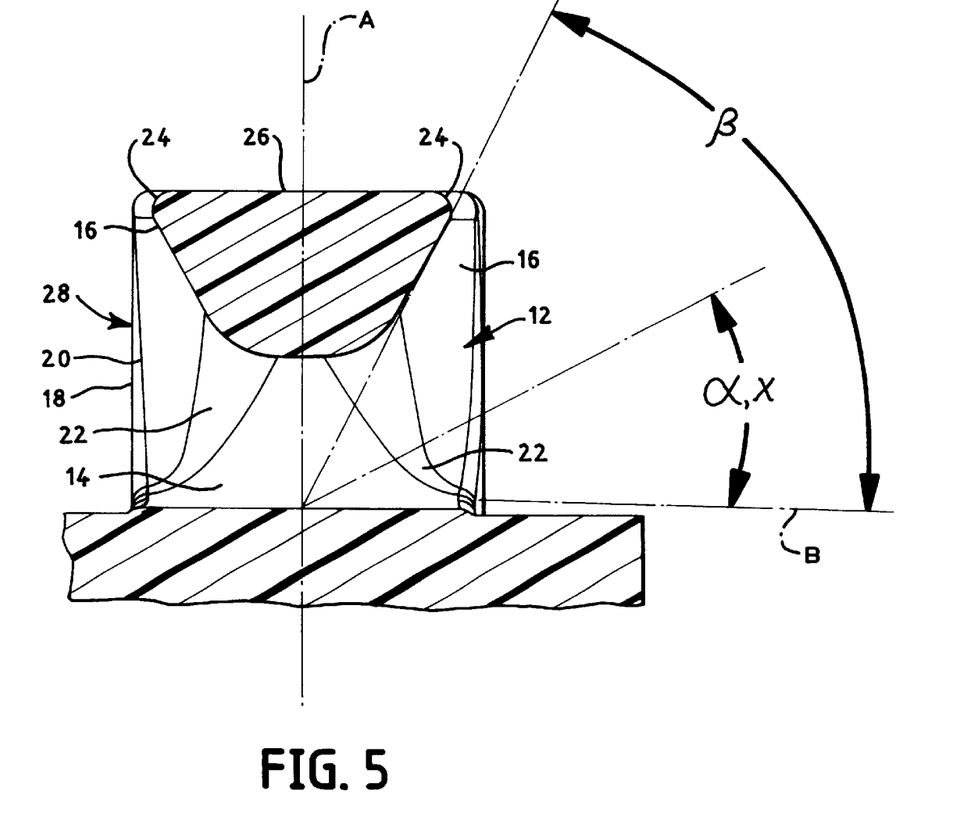
FIG. 5 is an enlarged sectional view of the suture anchor of FIG. 1 taken along line 5—5 of FIG. 3.
Figure 6:
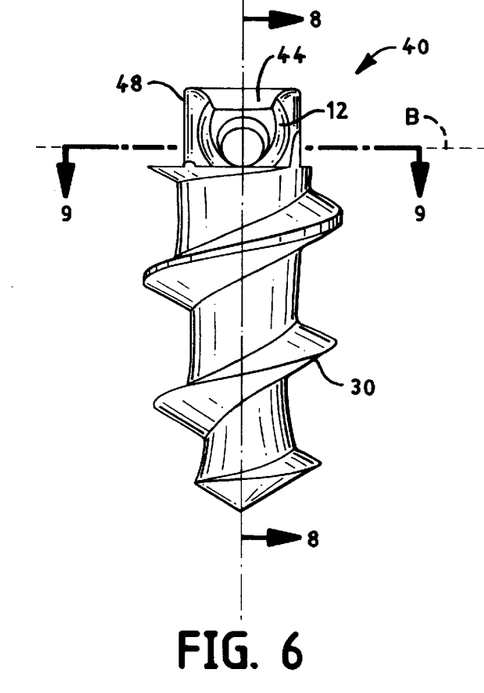
FIG. 6 is an elevation view of another suture anchor constructed in accordance with the present invention.
Figure 7:
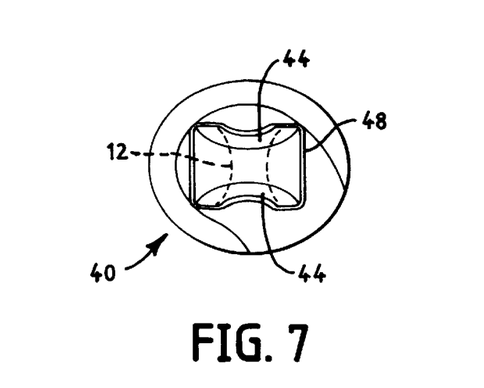
FIG. 7 is a top plan view of the suture anchor of FIG. 6.
Figure 8:
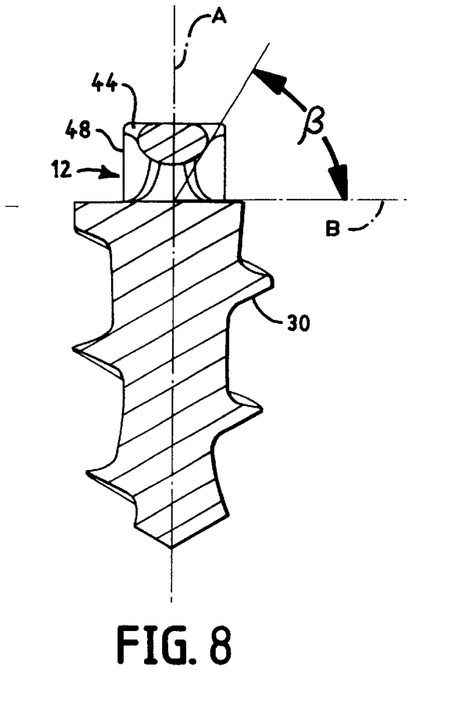
FIG. 8 is a sectional view of the suture anchor taken along line 8—8 of FIG. 6.
Figure 9:
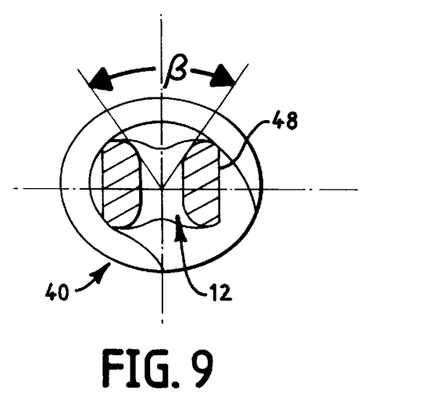
FIG. 9 is a sectional view of the suture anchor taken along line 9—9 of FIG. 6.
Figure 10:
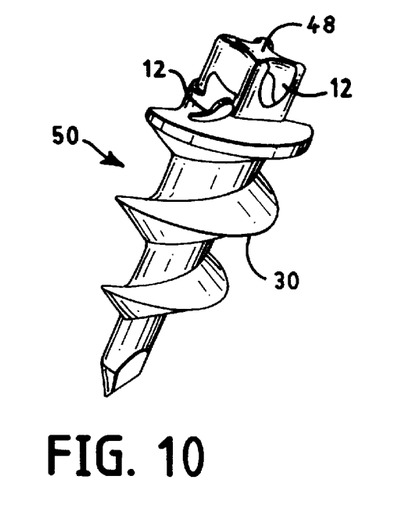
FIG. 10 is a perspective view of a further suture anchor constructed in accordance with the present invention.
Figure 11:
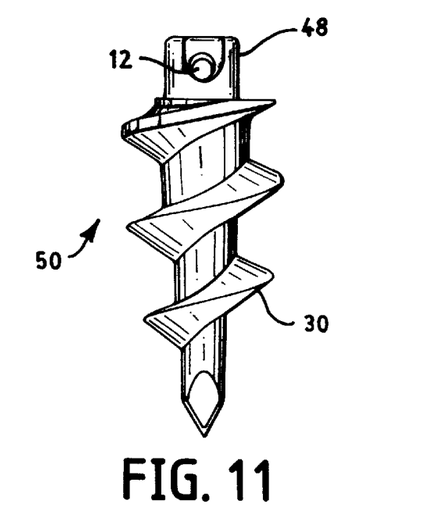
FIGS. 11 and 12 are elevation views of the suture anchor of FIG. 10, wherein the anchor has been rotated 90° between the two views.
Figure 12:
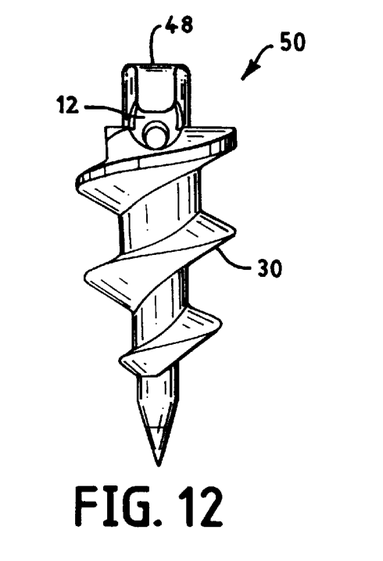
Figure 13:
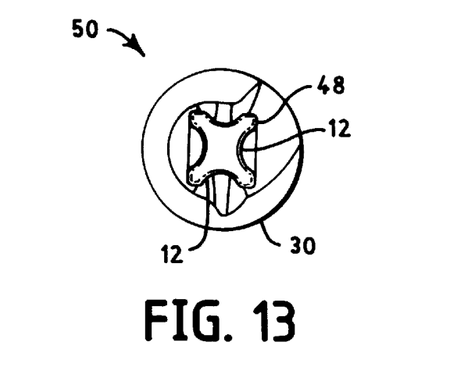
FIG. 13 is a top plan view of the suture anchor of FIG. 10.
Figure 14:
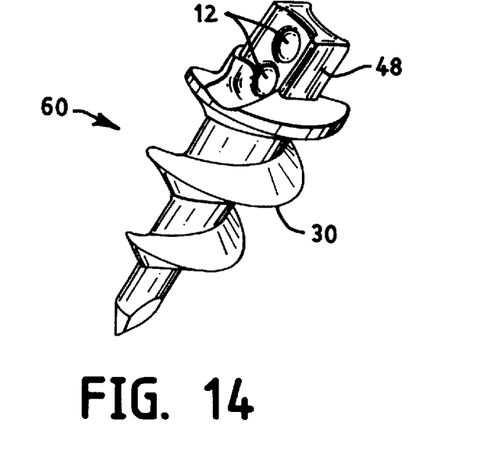
FIG. 14 is a perspective view of an additional suture anchor constructed in accordance with the present invention.
Figure 15:
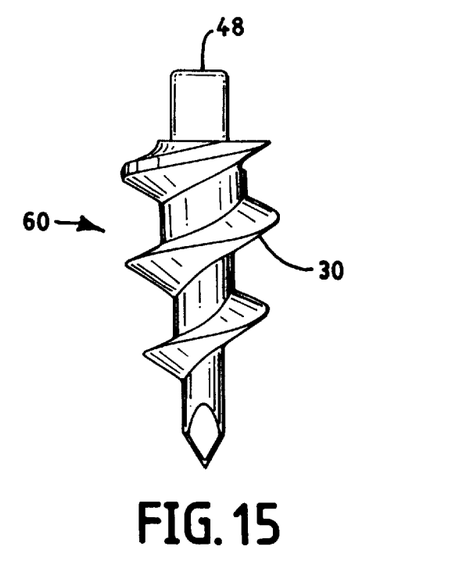
FIGS. 15 and 16 are elevation views of the suture anchor of FIG. 14, wherein the anchor has been rotated 90° between the two views.
Figure 16:
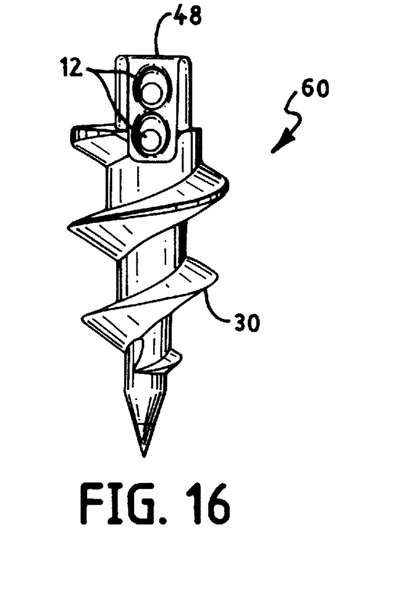
Figure 17:
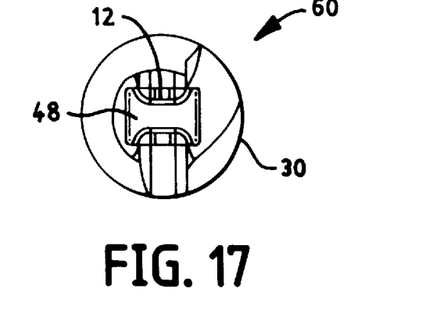
FIG. 17 is a top plan view of the suture anchor of FIG. 14.

The anchor 10 includes a body extending along the longitudinal axis "A" between a proximal end 1 and a distal end 2, and includes at least one eyelet 12 near the proximal end 1 extending between side or lateral surfaces 18 of the body, for receiving a suture. The eyelet 12 defines a central void region 14 extending substantially parallel with a lateral axis "B" of the body, and entry/exit void regions 16 extending between the side surfaces 18 of the body and the central void region 14. The defining surface of the central void region 14 is preferably cylindrical, but can be concave in other embodiments. The entry/exit void regions 16 each comprise a segment of a conic surface having an angle "β" and which extend towards the longitudinal axis "A" such that a cross-section of the eyelet 12 taken along a plane extending normal to the longitudinal axis "A" of the body, as illustrated by line 4—4 in FIG. 3, is substantially parabolic, as shown best in FIG. 4.

Preferably, an axis "C" of each entry/exit void region 16 extends within a plane formed by the longitudinal axis "A" and the lateral axis "B" of the body. In addition, the axes "C" of the entry/exit void regions 16 extend at an angle "α" with respect to the lateral axis "A" of the body, as shown best in FIGS. 2 and 5. Preferably, the angle "α" is about thirty degrees with respect to the lateral axis "B" of the body. As shown best in FIGS. 2 and 3, openings 20 of the eyelet 12 are elliptical due to the conic surface-like entry/exit void regions 16. In the preferred embodiment, the entry/exit void regions 16 each comprise a segment of a conic surface having an angle "β" equal to about sixty degrees.

The eyelet 12 optionally includes intermediate void regions 22 extending between the entry/exit void regions 16 and the central void region 14. Defining surfaces of the intermediate void regions 22 are preferably cylindrical. An axis "D" of each intermediate void region 22 extends within a plane formed by the longitudinal axis "A" and the lateral axis "B" of the body. In addition, the axes "D" of the intermediate void regions 22 extend at an angle "χ" with respect to the lateral axis "A" of the body, as shown best in FIGS. 2 and 5. Preferably, the angle "χ" is about thirty degrees with respect to the lateral axis "B" of the body. In the embodiment shown, therefore, the axes "D" of the intermediate void regions 22 are aligned with axes "C" of the entry/exit void regions 16.

The body of the anchor 10 also includes cut-outs 24 extending between the openings of the eyelet 12 and an end surface 26 of the body. The cut-outs 24 help to increase the angle of approach for a suture threaded through the openings 20 of the eyelet 12 and reduce stresses on the suture. Another embodiment of a suture anchor 40 constructed in accordance with the present invention is shown in FIGS. 6 through 9. The suture anchor 40 is similar to the suture anchor 10 of FIGS. 1 through 5, but includes enlarged cut-outs 44 that extend between the openings 20 of the eyelet 12 and corners formed by the end surface 26 and the side surface of the anchor 10.

Preferably all edges between the cut-outs 24 and the end surface 26, between the side surfaces 18 and the entry/exit void regions 16, between the entry/exit void regions 16 and the intermediate void regions 22, and between the intermediate void regions 22 and the central void region 14 are rounded, to further protect a suture threaded through the eyelet 12.

In the embodiment shown, the body of the anchor 10 includes a drive head 28 at one of the ends and the eyelet 12 is formed through the drive head. The drive head 28 preferably has a square or rectangular cross-section, as opposed to a hexagonal, circular or elliptical cross-section, because a square or rectangular cross-section has been found to provide more material for removal in order to provide the preferred eyelets 12. In the embodiment 10 of FIGS. 1–5, the drive head 28 has a square cross-section, while the embodiment 40 of FIGS. 6–9 has a drive head 48 having an eccentric rectangular cross-section.

As shown in FIG. 1, the body of the anchor 10 also includes an external threaded portion 30 extending between the drive head 28 and the other end of the body. The external threaded portion 30 can be self-tapping and can include a self-drilling tip if desired. The suture anchor 10 is made from a rigid and strong bio-compatible material. The suture anchor 10 can be constructed of a non-absorbable material such as titanium or stainless steel, or bio-absorbable material such as polymers, polyglycolic acid (PGA), poly-L-lactic acid (PLLA), polydioxanone (PDS), and poly-D,L-lactic acid (PDLLA), and their copolymers, tyrosine-derived polycarbonates and tricalcium phosphates. The bio-absorbable anchors are useful when the eyelet is deployed below the surface of a bone so that bone regrowth eventually takes over to hold the suture to the bone as the anchor is absorbed.

The suture anchors 50, 60 of FIGS. 10 through 17 are similar to the suture anchor 40 of FIGS. 6 through 9, but each anchor 50, 60 includes two eyelets 12. In the embodiment 50 of FIGS. 10 through 13, the two eyelets 12 are perpendicular, while in the embodiment 60 of FIGS. 14 through 17 the eyelets 12 are parallel.

Figure 18:
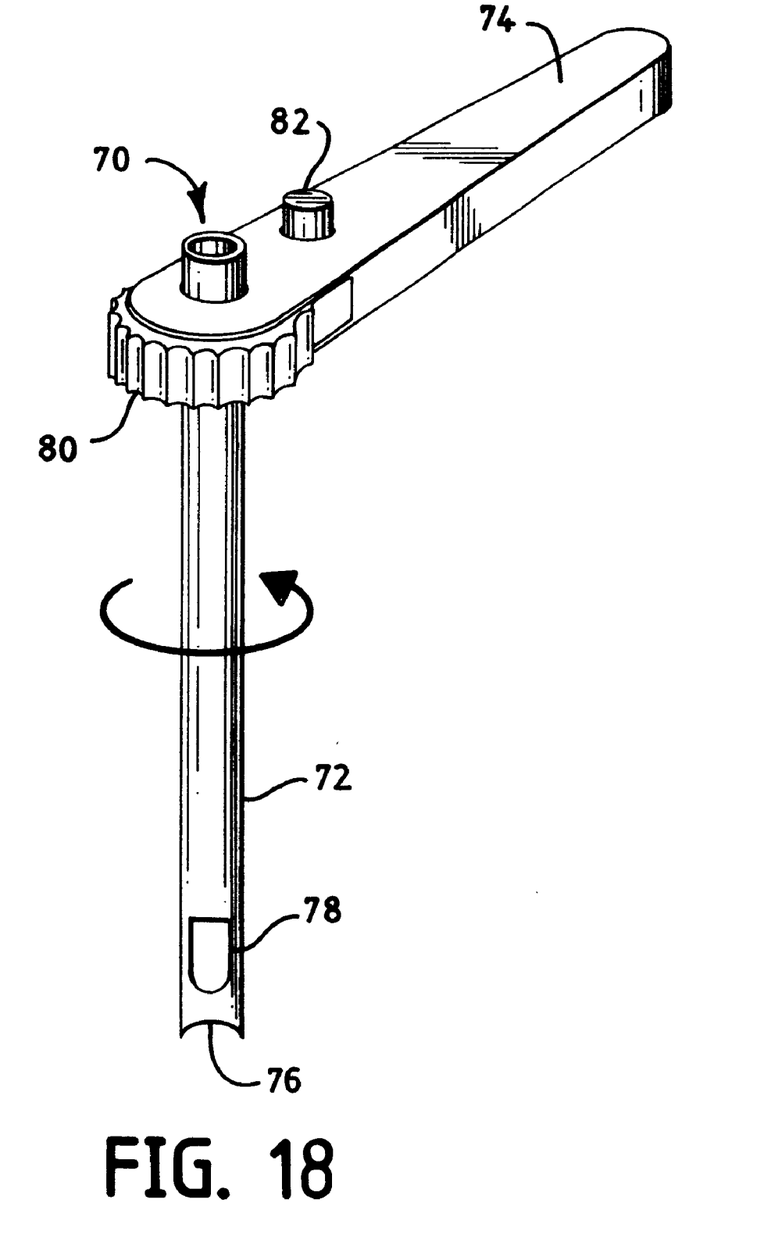
FIG. 18 is a perspective view of a drill guide constructed in accordance with the present disclosure.

FIG. 18 is a perspective view of a drill guide 70 constructed in accordance with the present disclosure. The drill guide 70 is for assisting in positioning a drill bit while drilling a hole in bone for receiving a suture anchor during an arthroscopic surgical procedure, such as shoulder arthroscopy. The drill guide 70 includes a tubular guide shaft 72 extending through a handle 74. The shaft 72 is for extending into the shoulder joint, for example, such that a tip 76 of the shaft can be positioned on the glenoid rim of the scapula bone of the shoulder joint, and includes a window 78 near the tip for properly aligning the shaft with the rim. The shaft 72 receives a drill bit therethrough for drilling a hole within the scapula. The shaft 72 can also be used to help position an anchor in the drilled hole and secure a suture to the anchor.

As shown, the drill guide 70 includes an adjustment wheel 80 secured to the shaft 72 within the handle 74 such that turning the wheel rotates the shaft to a desired position. The guide 70 also includes a button 82 in the handle 74 for preventing rotation of the wheel 80 and the shaft 72 when the button is moved within the handle to maintain the shaft in the desired position.

Figure 19:
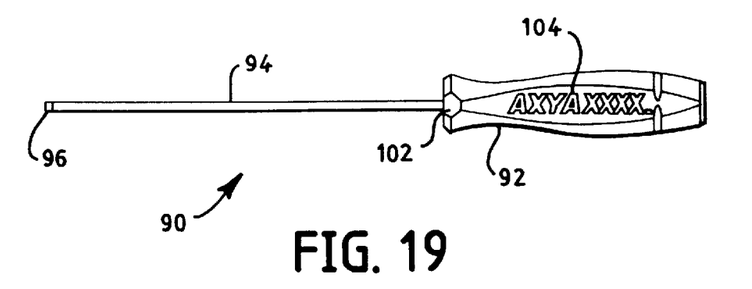
FIG. 19 is a side elevation view of a drive tool constructed in accordance with the present disclosure for use with the suture anchor of FIG. 1.
Figure 20:
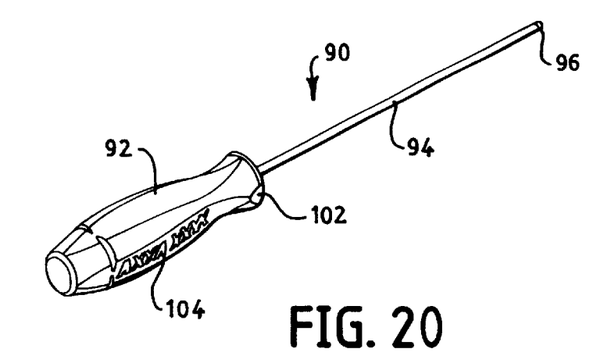
FIG. 20 is a perspective view of the drive tool of FIG. 19.

FIGS. 19 and 20 show a tubular drive tool 90 constructed in accordance with the present invention. The tool 90 is for use in driving a suture anchor 10 into bone, while a suture 200 threaded through an eyelet 12 of the anchor extends through the hollow tool 90. The tool 90 includes a handle 92, a tube 94 extending from the handle to a distal end, and a drive socket 96 attached to the distal end of the tube.

Figure 21:
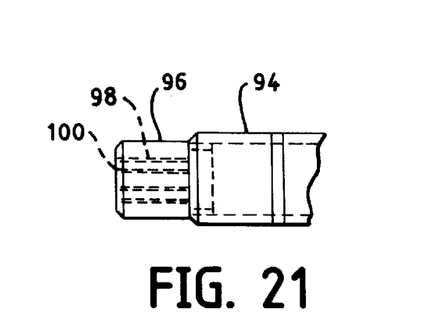
FIG. 21 is an enlarged elevation side view of a tip of the drive tool of FIG. 19.
Figure 22:
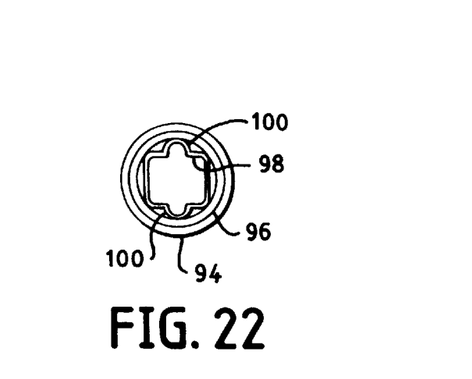
FIG. 22 is an enlarged elevation end view of the tip of the drive tool of FIG. 19.

As shown in FIGS. 21 and 22, the drive socket 96 includes inwardly facing surfaces 98 for gripping outwardly facing surfaces of the drive head 28 of the suture anchor 10 for transferring torque from the drive tool 90 to the suture anchor 10. In addition, the inwardly facing surfaces 98 include recesses 100 positioned for alignment with the entry/exit void regions 20 of the eyelets 12 of the anchor 10 and sized to receive a suture 200 passing through the eyelet. In the embodiment shown, the drive socket 96 is permanently attached to the tube 94, but can be provided as removably attachable to the tube.

As shown in FIGS. 19 and 20, the handle 92 of the drive tool 90 includes reference markings 102, 104 aligned with the recesses 100 of the drive socket 96. In the embodiment shown, the reference marks include lettering 104 and flat portions 102 formed on the handle 92. The reference marks 102, 104 help to identify the orientation of a suture 200 extending through the anchor 10 to improve suture and soft tissue alignment while placing the anchor.

Figure 23:
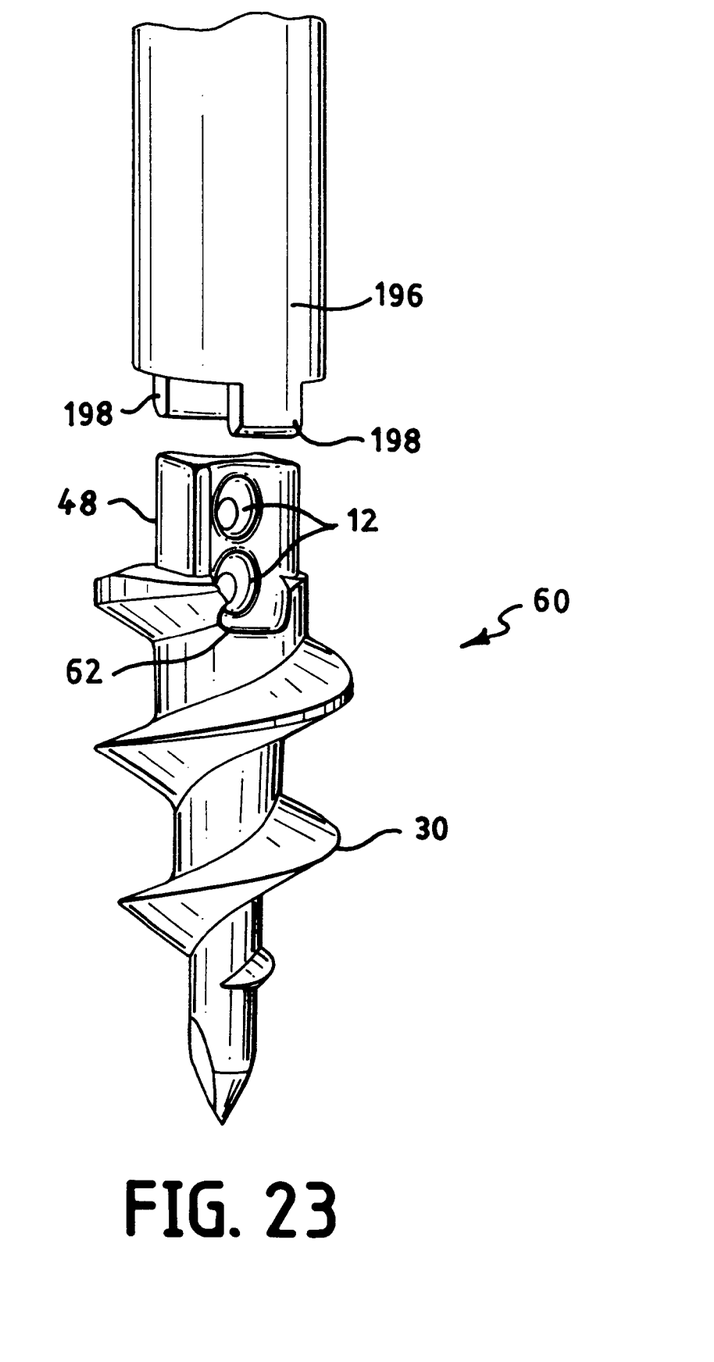
FIG. 23 perspective view of another tip of a drive tool constructed in accordance with the present disclosure shown being used with, for example, the suture anchor of FIG. 14.

FIG. 23 shows another drive socket 196 constructed in accordance with the present disclosure. The drive socket 196 is similar to the drive socket 96 of FIGS. 21 and 22, but further includes at least two tabs 198 extending axially from a distal edge of the socket. The tabs are for covering and protecting a suture (not shown) received in the anchor 60, while the anchor is being screwed into a bone using the socket 196. As shown, the suture anchor 60 includes an axially extending recess 62 extending over each opening of the entry/exit void regions of the eyelet 12 and the tabs 198 are aligned for receipt within the recesses 62 and adapted to receive a suture between the tabs 198 and the anchor 60, so that the suture is not crushed or otherwise damaged between the socket and the anchor.

The suture anchors, drill guide and drive tool described above can be included as part of a surgical kit also including at least one length of suture (not shown) for every suture anchor. The suture can be a monofilament or multifilament, braided suture. The suture is bio-compatible and can be bio-absorbable if desired. In addition, one end of the length of suture is preferably deformed and shaped differently than the other end, such that a surgeon can distinguish the two ends of the suture length visually and by touch during a surgical procedure. For example, one end of the length of suture can be deformed and shaped so that it is flat, while the other end is not deformed such that it remains cylindrical.

It should be understood that the presently disclosed suture anchors, drill guide and driver tool can be embodied in other specific forms without departing from the spirit or essential characteristics thereof. For example, for all embodiments of the suture anchors disclosed herein, the anchor can be comprised of a suitable metal or plastic. Furthermore, any plastics used can be of the type that dissolve in the body in a harmless manner a suitable period after being secured therein, such that the suture anchors and sutures do not have to be removed by a medical person. In addition, an eyelet formed in accordance with the present invention can be formed in an insert for insertion into an anchor after the anchor has been fixed within a bone, as opposed to being formed directly in the anchor. The present embodiments, therefore, are to be considered in all respects as illustrative and not restrictive, the scope of the invention being indicated by the appended claims rather than by the foregoing description. All changes that come within the meaning and range of he equivalency of the claims are therefore intended to be embraced therein.

What is claimed is:

1. A suture anchor for securing soft tissue to bone, comprising:
   a body extending from a proximal end to a distal end along a longitudinal axis; and
   at least one eyelet extending between opposite lateral surfaces of the body for receiving a suture, the eyelet defining,
   two entry/exit void regions, each entry/exit void region extending from one of the lateral surfaces of the body, having a central axis forming an acute angle with the longitudinal axis of the body, and having a surface comprising a segment of a conic surface extending about the axis of the entry/exit void region and tapering inward towards the longitudinal axis of the body, and
   a central void region extending between the entry/exit void regions along an axis of the central void region extending transverse to the longitudinal axis of the body.

2. A suture anchor according to claim 1, wherein edges between the entry/exit void regions and the central void region and between the entry/exit void regions and the lateral surfaces are rounded.

3. A suture anchor according to claim 1, wherein the axis of each entry/exit void region extends within a plane formed by the longitudinal axis of the body and the axis of the central void region.

4. A suture anchor according to claim 3, wherein the axes of the entry/exit void regions extend at equal angles.

5. A suture anchor according to claim 4, wherein the axes of the entry/exit void regions extend at an angle of about sixty degrees with respect to the longitudinal axis of the body.

6. A suture anchor according to claim 1, wherein openings of the eyelet are elliptical.

7. A suture anchor according to claim 1, wherein the body includes a drive head at one of the ends and the eyelet is formed through the drive head.

8. A suture anchor according to claim 7, wherein the cross-section of the drive head is substantially rectangular.

9. A suture anchor according to claim 1, wherein the body includes cut-outs extending between openings of the eyelet and an end surface of the body.

10. A suture anchor according to claim 9, wherein each of the cut-outs extends between corners formed by the end surface and the lateral surface of the body.

11. A suture anchor according to claim 1, wherein the surfaces of the entry/exit void regions each comprise a segment of a conic surface of about sixty degrees.

12. A suture anchor according to claim 1, wherein the at least one eyelet comprises two eyelets.

13. A suture anchor according to claim 12, wherein the eyelets are substantially parallel.

14. A suture anchor according to claim 12, wherein the eyelets are non parallel.

15. A suture anchor according to claim 1, wherein the body includes an external threaded portion extending towards one of the ends of the body.

16. A suture anchor according to claim 15, wherein the external threaded portion is self-tapping.

17. A suture anchor according to claim 15, wherein the external threaded portion includes a self-drilling tip at the end of the body.

18. A suture anchor according to claim 1, made from bio-compatible material.

19. A suture anchor according to claim 1, made from bio-absorbable material.

20. A suture anchor according to claim 1, wherein the central void region is cylindrical.

21. A suture anchor according to claim 1, wherein the eyelet further includes intermediate void regions extending between the entry/exit void regions and the central void region.

22. A suture anchor according to claim 21, wherein the intermediate void regions are cylindrical.

23. A suture anchor according to claim 21, wherein an axis of each intermediate void region extends within a plane formed by the longitudinal axis of the body and the axis of the central void region.

24. A suture anchor according to claim 23, wherein the axes of the intermediate void regions extend at an angle with respect to the longitudinal axis of the body.

25. A suture anchor according to claim 24, wherein the axes of the intermediate void regions extend at an angle of about sixty degrees with respect to the longitudinal axis of the body.

26. A suture anchor according to claim 23, wherein the axes of the intermediate void regions are aligned with the axes of the entry/exit void regions.

27. A kit including a suture anchor according to claim 1, and further comprising a drill guide having:
- a handle;
- a hollow guide shaft rotatably secured to the handle, the guide shaft having a tip and an alignment window adjacent the tip;
- adjustment wheel radially extending from the shaft; and
- a button positioned within the handle and movable to a locked position preventing rotation of the adjustment wheel.

28. A kit according to claim 27, further including at least one length of suture.

29. A kit according to claim 28, wherein the suture is a monofilament.

30. A kit according to claim 28, wherein one end of the length of suture is deformed.

31. A kit according to claim 28, wherein the suture is bio-compatible.

32. A kit according to claim 31, wherein the suture is bio-absorbable.

33. A kit including a suture anchor according to claim 1, wherein the body of the suture anchor includes a drive head at one of the ends and the eyelet is formed through the drive head, and the kit further comprises a tubular drive tool having:
- a handle;
- a tube extending from the handle to a distal end; and
- a drive socket attached to the distal end of the tube and including inwardly facing surfaces for gripping outwardly facing surfaces of the drive head of the suture anchor for transferring torque from the drive tool to the suture anchor, and wherein the inwardly facing surfaces include recesses positioned for alignment with the entry/exit void regions of the eyelet of the anchor and sized to receive a suture passing through the eyelet.

34. A kit according to claim 33, wherein the handle of the drive tool includes reference markings aligned with the recesses of the drive socket.

35. A kit according to claim 33, wherein the drive socket is removably attached to the tube.

36. A kit according to claim 33, further including at least one length of suture.

37. A kit according to claim 36, wherein the suture is a monofilament.

38. A kit according to claim 36, wherein one end of the length of suture is deformed.

39. A kit according to claim 36, wherein the suture is bio-compatible.

40. A kit according to claim 39, wherein the suture is bio-absorbable.

41. A kit according to claim 33, wherein the drive socket further includes at least two tabs extending axially from a distal edge of the socket.

42. A kit according to claim 41, wherein the suture anchor includes an axially extending recess extending over each opening of the entry/exit void regions of the eyelet for receiving the tabs of the drive socket.

43. A kit including a suture anchor according to claim 1, wherein the body of the suture anchor includes a drive head at one of the ends and the eyelet is formed through the drive head, and an axially extending recess extending over each opening of the entry/exit void regions of the eyelet and the kit further comprises:
- a tubular drive tool having a drive socket including inwardly facing surfaces for gripping outwardly facing surfaces of the drive head of the suture anchor, and at least two tabs extending axially from a distal edge of the socket and adapted for receipt within the axially extending recesses of the anchor and adapted to receive a suture between the tabs and the anchor.

* * * * *